United States Patent [19]

Mehra et al.

[11] Patent Number: 5,643,591
[45] Date of Patent: Jul. 1, 1997

[54] SOLID DOSAGE FORMS

[75] Inventors: Dev K. Mehra, Furlong, Pa.; Nagui I. Ibrahim, East Windsor, N.J.; Edwin G. Fleck, Jr., Newark, Del.

[73] Assignee: FMC Corporation, Philadelphia, Pa.

[21] Appl. No.: 230,407

[22] Filed: Apr. 20, 1994

Related U.S. Application Data

[63] Continuation-in-part of Ser. No. 814,186, Dec. 19, 1991, abandoned, which is a continuation-in-part of Ser. No. 642,099, Jan. 16, 1991, abandoned.

[51] Int. Cl.$^6$ .................................................. A01N 25/12
[52] U.S. Cl. ................. 424/408; 424/409; 424/464; 424/465
[58] Field of Search .......................... 424/408, 465, 424/494, 710; 504/116; 71/65, 64.03–64.06, 64.13; 514/588; 106/163.1, 177, 186, 197.2

[56] References Cited

U.S. PATENT DOCUMENTS

| | | | |
|---|---|---|---|
| 3,558,299 | 1/1971 | Baskin | 71/28 |
| 3,951,821 | 4/1976 | Davidson | 252/1 |
| 4,056,615 | 11/1977 | Vora et al. | 424/120 |
| 4,249,938 | 2/1981 | Takemoto et al. | 71/98 |
| 4,517,179 | 5/1985 | Raghunathan | 514/249 |
| 4,517,381 | 5/1985 | Takematsu et al. | 564/207 |
| 4,681,765 | 7/1987 | Guley | 424/456 |
| 4,744,987 | 5/1988 | Mehra et al. | 424/156 |
| 4,816,064 | 3/1989 | Konno et al. | 71/93 |
| 4,820,522 | 4/1989 | Radebaugh et al. | 424/468 |
| 4,857,336 | 8/1989 | Khanna et al. | 424/473 |
| 4,931,285 | 6/1990 | Edgren et al. | 424/473 |

FOREIGN PATENT DOCUMENTS

| | | |
|---|---|---|
| 786632 | 7/1972 | Belgium . |
| 0128482 | 12/1984 | European Pat. Off. . |
| 0167191 | 8/1986 | European Pat. Off. . |
| 7237012 | 9/1970 | Japan . |
| 59082303 | 2/1982 | Japan . |
| 7543585 | 4/1985 | Japan . |

*Primary Examiner*—Neil S. Levy
*Attorney, Agent, or Firm*—Patrick C. Baker; Jordan J. Driks; Robert D. Jackson

[57] ABSTRACT

A composition for agricultural and other actives, comprising a finely-divided particulate combination of microcrystalline cellulose, at least one nitrogen compound such as urea, an ammonium sulfate or phosphate and, optionally, a suspending agent for the microcrystalline cellulose. The composition can be compacted to form shaped, solid dosage forms such as tablets which disintegrate rapidly in an aqueous medium.

12 Claims, No Drawings

SOLID DOSAGE FORMS

RELATED APPLICATION

This application is a continuation-in-part of Ser. No. 814,186, filed Dec. 19, 1991, now abandoned, which is a continuation-in-part of Ser. No. 642,099, filed Jan. 16, 1991, now abandoned.

FIELD OF THE INVENTION

This invention relates to solid dosage forms, particularly compacted solid dosage forms containing microcrystalline cellulose.

BACKGROUND OF THE INVENTION

It is the common practice to manufacture solid dosage forms in which the ingredients, i.e., active agents, excipients, etc. are compacted into various shapes such as tablets, briquettes, pellets and the like. Because of its excellent compression properties, a preferred excipient is microcrystalline cellulose (MCC). Compacted solid dosage forms made with MCC are durable and stable yet readily disintegrate when added to an aqueous medium with concomitant release of active components.

MCC, however, is a relatively expensive excipient. Consequently, its application in compression molding formulation has been confined largely to high cost items such as pharmaceutical tablets. It has not, for instance, proved economically feasible to utilize MCC in preparing solid dosage forms of agricultural chemicals, e.g., insecticides, herbicides, fungicides, etc. which are considerably lower per unit price than pharmaceuticals.

According to U.S. Pat. No. 4,744,987 issued to Mehra et al, a coprocessed blend of MCC and calcium carbonate is similar in its compression molding characteristics to MCC along only less expensive. The product was developed for preparing pharmaceutical solid dosage forms.

SUMMARY OF THE INVENTION

It has now been discovered that a finely-divided homogeneous particulate blend of MCC and a nitrogen compound selected from the group consisting of urea, ammonium sulfate and ammonium phosphate in which the weight ratio of MCC to nitrogen compound is from about 10:1 to about 1:10 is an effective low cost excipient for producing compacted solid dosage forms and the provision of said homogeneous blend and solid dosage forms made therewith constitute the principal objects and purposes of the invention.

DETAILED DESCRIPTION

The particulate blend of the invention is prepared by combining the MCC and nitrogen compound preferably urea in any suitable manner for mixing particulate materials. These include dry blending or granulation, wet granulation followed by oven drying and aqueous dispersion followed by spray drying. Such mixing techniques are well known in the art.

Solid dosage forms are prepared by mixing the particulate blend herein with active agent plus any ancillary ingredients and the resulting mixture compacted into the desired shape such as tablets, pellets, beads, balls, bars, disks and briquettes.

The particles size of the MCC influences the behavior and properties of the compacted shape. For instance, if the shape is fabricated by tabletting, a feed material containing a preponderance of small MCC particles—average size about 10–20 microns—will flow poorly in the tabletting machine and tend to clog the hopper or feed mechanisms. However, tablets containing the small size MCC particles provide a more uniform and stable suspension upon disintegration of the tablet in an aqueous medium. On the other hand, a feed containing larger MCC particles—average size about 90 microns and larger—will flow better in the tabletting machine.

In general, a particulate blend containing MCC in the size range of from about 20–90 microns, preferably about 30–70 microns and most preferably about 50 microns affords a satisfactory combination of compression properties and dissolution characteristics.

Desirably, the nitrogen compound or mixtures thereof consists of a free flowing finely-divided particulate material. Where urea is the nitrogen compound, the industrial grade product is suitable such as urea ground to 8–10 mesh, a coarse material, or a finer 15–30 mesh, the mesh sizes being USS. Small particle size (of the order of about 10–200 microns) is achieved by well-known techniques including crystallization, freeze drying, and various milling processes. These can be applied to the individual components of the blend or to the dry blend itself. If the nitrogen compound is wet granulated with the active agent to form the finished dosage form, the nitrogen compound will dissolve into the MCC. In this case, particle size of the nitrogen compound is not important.

The ratio of MCC to nitrogen compound along with particle size, influences the hardness (as measured by tensile strength) of solid dosage forms prepared from the particulate blend, and the hardness in turn affects the disintegration rate of the forms. For example, tablets should be hard enough to resist chalking and breaking during normal handling but readily disintegrate in an aqueous medium. Tablets with a tensile strength in the range of about 2–25 kg/cm$^2$ will resist breaking during normal handling and will disintegrate quickly in an aqueous medium. A preferred tensile strength is about 3–15 kg/cm$^2$, most preferred about 3–10 kg/cm$^2$. Suitable MCC:nitrogen compound ratios for such purposes are from about 10:1 to about 1:10 by weight, preferably about 5:1 to about 1:5, most preferably about 1:1.

The components of the herein particulate blend are combined in any suitable manner to produce a dry, finely-divided material or powder. Blending techniques are well known and include dry blending or granulation, wet granulation followed by oven drying, and aqueous dispersion followed by spray drying. Dosage forms may be produced from the blend and active agent by any of the known compacting processes, including direct compression and/or roller compaction of dry blends, wet granulation followed by compaction, and/or spheronization.

When tabletting is the method selected for producing the solid dosage forms, conventional dry granulation, wet granulation, direct compression, spheronization or spray drying may be used to prepare the particulate blend for tabletting. The selection of method depends primarily on the active agent, the ability of the mixture of nitrogen compound and active to flow freely in the tabletting machine or extruder, and the cohesiveness of the ingredients. If the active agent can be admixed with the nitrogen compound to produce a free flowing, dense powder, the mixture can be directly compressed. In dry granulation, a dry powdery blend of the nitrogen compound components and active agent is compressed to form slugs if a tablet press is used.

Alternatively, the dry blend is roller compacted into sheets. The slugs or sheets are then sieved (for example, to 12, 14 or 16 USS mesh) to form densified granules for final tabletting.

In one mode of wet granulation, water is added to a mixture of the MCC and nitrogen compound to form a wet, granular material. The amount of water depends on the ratio of MCC to nitrogen compound. The higher the MCC:nitrogen compound ratio by weight, the greater will be the amount of water which can be tolerated. Generally, about one-third of the mixture of MCC:nitrogen compound and water will be water when the MCC:nitrogen compound is about 1:1 by weight. The wet, granular material is screened (to 10 USS mesh, for example), dried, and again screened (to 20 USS mesh, for example). The granules are then ready for admixture with the active agent and other tabletting ingredients, if any.

In a variation of the wet granulation process, the MCC may be "coprocessed" with the nitrogen compound in the manner described in the aforecited U.S. Pat. No. 4,744,987 where the nitrogen compound of the invention is substituted for the calcium carbonate of the patent. In "coprocessing", a uniform aqueous slurry of the MCC and nitrogen compound is formed with good agitation and the slurry is dried in any effective manner. Spray drying is preferred. MCC:nitrogen compound ratios may be the same as in other blending methods and the particulate product may be screened as needed to obtain a desired particle size distribution. The coprocessed material may then be combined with an active agent in the same manner as described above with respect to dry or wet granulation and direct compression.

Wet granulation or extrusion can be used to prepare particulate blends for all active agents except those which are sensitive to water.

In another, optional, aspect of the invention, it has been found that the MCC can be prevented from settling out when solid dosage forms of the invention are dispersed in aqueous media by incorporating into the particulate blend a minor amount of a hydrocolloid compatible with the MCC and effective for assisting in wetting out (hydrating) the MCC. Such agents thus act to suspend the MCC and are further characterized by water solubility and by bonding or otherwise adhering to the MCC. They may be natural or synthetic and generally are polymeric carbohydrates.

Typical of the suspending agents are cellulose derivatives such as sodium carboxymethylcellulose, hydroxyethylcellulose, hydroxypropyl cellulose, hydroxypropyl methylcellulose and methylcellulose; gums such as seaweed extracts (agar, carrageenan, alginates), plant extracts (pectins, low methoxy pectins), plant exudates (arabic, tragacanth, karaya, ghatti), plant seed extracts (locust bean, guar), and microbial fermentation gums (dextran, xanthan); starches including pregelatinized and modified starches; and synthetics such as the carboxyvinyl polymers solid under the brand name "Carbopol".

The preferred suspending agents are salts such as sodium carboxymethylcellulose. While not fully understood, it is believed that best suspending action results from particle repulsion forces due to the ionic character of such materials.

The suspending agents are used in small amounts, of the order of about 0.05–25% by weight of the MCC, preferably about 0.5–10% by weight, taking into account the molecular weight and correlative viscosity of the agents. In the case of the preferred agent, sodium carboxymethylcellulose, medium or high viscosity materials are preferred due to the higher rate of hydration of these materials, although the lower viscosity materials will disperse more readily.

The suspending agent may be admixed with the MCC and nitrogen compound in any effective manner and the order of addition is not critical. If the particulate blend herein is prepared from aqueous dispersion, e.g., by wet granulation or spray drying, the suspending agent is usually added after admixture of the MCC and nitrogen compound in the aqueous medium, with agitation effective for uniform admixture.

Various ingredients well-known to formulators of solid dosage forms can be added to the particulate blend of the invention to enhance the blending, shaping and/or disintegration processes. These include lubricants, glidants, dispersants, surfactants, disintegrants, and fillers or auxiliary binders, and are employed in relatively small amounts, less than about 20% by weight of the solid dosage form, more usually less than about 10% by weight. The choice of additive and amount are matters of routine consideration and trial for the skilled formulator.

Lubricants facilitate the ejection of compacted forms from a die cavity. They may also reduce interparticle friction (glidant functionality) and prevent adhesion of materials to die and punch surfaces (anti-adherent properties). Typical lubricants are talc; long chain fatty acid esters or salts thereof such as stearic and palmitic acids, and magnesium or calcium stearate; and other materials such as hydrogenated vegetable oils, glyceryl palmitostearate, gyceryl benzoate, and polyethylene glycol 6000. Glidants are limited to improvement of the flow properties of powders and granules, and include materials such as aerogenic silica, fumed silicon dioxide and silica hydrogel. Typical use levels of lubricants and glidants are about 0.25–5 weight percent of each, based on total dosage form weight.

Auxiliary disintegrants may be included in the particulate blend to increase the breakup rate of the solid dosage forms in an aqueous medium, particularly at low temperatures. Typical disintegrants are starch (corn, potato, amylose), sodium starch glycolate, alginic acid, synthetic polymers such as styrene-divinyl-benzene or acrylic ion exchange or adsorbent resins, crosspovidone, and soy polysaccharides. A preferred disintegrant is croscarmellose, a cross-linked sodium carboxymethylcellulose sold under the trademark "Ac-Di-Sol". The disintegrants typically are used at levels of about 1–5 weight percent based on total dosage form weight.

The active agents to be delivered with the particulate blend of the invention include any liquid or solid compounds or mixtures of compounds which are to be eventually dispersed or dissolved in an aqueous medium including an industrial process or waste stream, a body of water such as a river or lake, a fluid bed, a swimming pool, an oil well, a body fluid, an aqueous food, food supplement or pharmaceutical, and the like). Of course, the active agent must not be reactive with the components in the particulate blend in a manner that reduces or interferes with the properties of the blend. The particulate blend and solid dosage form of the invention, therefore, have application to a wide variety of fields and products, including agricultural and veterinary products, pharmaceuticals, animal and human foods, swimming pool additives, industrial biocides for oil wells and other applications, cosmetics, household pesticides, and dye manufacturing.

In the agricultural field, the active agents include herbicides, plant growth regulators, and biocides of all types, such as pesticides. The pesticides include atrazine, benazone, trifluralin, propanil, metribuzin, alachlor, butachlor, bromoxynil, clomazone, oxadiazon, lorsban, bifenox, aldicarb, monoorotophos, propoxur, diflubenzuron, carbofuran, permethrin, carbaryl, cypermethrin, endosulfan, cyfluthrin, bifenthrin, terbufos, fenamiphos, cadusafos, paclobutrazol, glyphosine, giberellic acid, and the like.

The particulate blend of the invention permits great flexibility in dosage form design. For example, compressed forms such as tablets can be produced in bisected or multisected form so that they can be subdivided by hand or machine for delivery of fractional amounts of active agent. Such tablets are particularly useful for delivery of pesticides, herbicides and other agricultural chemicals for home and garden, green house, forestry, and farm markets without significantly compromising bioefficacy. Furthermore, chemically incompatible actives, such as tablets containing several different pesticides or combinations of herbicides and pesticides, can be separated in the solid dosage forms by forming multilayers using known techniques.

By virtue of the invention, the benefits of MCC in solid dosage forms are now made available to delivery of active agents in applications where cost is a significant factor. This is achieved along with surprisingly improved properties, including rapid disintegration, and no diminution of properties attributable to the MCC. The property of rapid disintegration even at low ambient temperature (such as the dew point in agricultural environments) reduces arian toxicity when the active agent is a type which would present such risk if broadcast in slow disintegrating granules or extrudate form. In addition, because the carrying capacity of the particulate blend of the invention is very high, as much as 65% by weight or more of active agent in some cases, the cost effectiveness of the composition is further enhanced.

The following examples will further illustrate the invention without limiting the scope and spirit thereof, it being understood that the invention is entitled to the full scope and range of equivalents indicated in the appended claims.

EXAMPLE 1

Dry-Blend Process

AVICEL® PH 105 microcrystalline cellulose (MCC, 20 microns average particle size, FMC Corporation) and urea granules (milled to 20–60 USS mesh) were dry-blended in a PK mixer to form five blends of different proportions (Table 1). Four grams of each blend was used to prepare 2.54 cm diameter tablets in a Carver tablet press operated at 923 kg/cm$^2$ compression force, 3% moisture content. Each tablet was measured for thickness. The disintegration time was determined by immersing each tablet into 400 mL of room temperature tap water. The results are presented in Table 1. It can be seen that as compared with the controls, disintegration times were substantially reduced by the presence of urea.

TABLE 1

| Tablet Composition | Thickness of | Disintegration Time$^a$ |
|---|---|---|
| % wt/wt MCC/urea | Tablet (mm) | (sec) |
| 100/0 (control) | 6.44 | 240 |
| 66.6/33.4 | 7.32 | 90 |
| 50/50 | 6.82 | 15 |
| 25/75 | 6.41 | 30 |
| 0/100 (control) | 6.32 | no disintegration |

$^a$Disintegration time was measured from when the tablet began to disintegrate to when the tablet had fully disintegrated.

EXAMPLE 2

Wet Granulation Process

Urea (particle size same as Example 1) and AVICEL® PH 105 microcrystalline cellulose (MCC, 150 grams) were mixed in a Hobart mixer for five minutes to form a 1:1 urea/MCC blend. Approximately 150 mL to tap water was added during mixing, forming a wet, granular material. This material was screened using a 10 USS mesh screen. The resulting granular material was dried in an oven at 50° C. until a moisture level of 3% was obtained. The dry, granular material was screened using a 20 USS mesh screen. These granules were used to prepare 0.5 gram tablets using a Stokes B2 model tablet press and 7/16 inch standard concave punches. Tablet hardness was measured on a Schleuniger Hardness Tester. Tablet disintegration time was determined by immersing each tablet in approximately 400 mL of water at room temperature. The results are shown in Table 2 from which it will be seen that the harder tablets (tensile 10.5 kg/cm$^2$) nevertheless disintegrate in the same time as the softer tablets (tensile 6 kg/cm$^2$), but that increasing the hardness substantially retards or prevents disintegration.

TABLE 2

| Tablet Compression Force (kg) | Tablet Tensile$^a$ Strength (kg/cm$^2$) | Disintegration$^b$ Time (sec) |
|---|---|---|
| 190 | 6 | 10 |
| 380 | 10.5 | 10 |
| 700 | 31 | no disintegration$^c$ |
| 1050 | 35 | no disintegration$^c$ |

$^a$Tablet tensile strength was calculated according to the following formula: TS = $2H/\pi DT$, in which H = tablet hardness (kg), D = tablet diameter (cm), and T = tablet thickness (cm)
$^b$Disintegration time was measured form the moment the tablet was immersed in the water until it had fully disintegrated.
$^c$Tablet did not disintegrate within five minutes.

EXAMPLE 3

Herbicide Tablets Prepared by Dry Granulation

A mixture of 4.15 kg of atrazine herbicide, 45.4 g of Ac-Di-Sol® croscarmellose disintegrant (FMC Corporation), 226.8 g of a sodium lignosulfonate anionic dispersant, 45.4 g of an alkylarylsulfonate surfactant, and 68.0 g of an aerogenic synthetic silica were mixed in a PK blender for ten minutes. The resultant blend was milled in a Fitz mill at a rate of one pound per minute using a 0.02 inch opening screen. A portion of the milled material (1.34 kg) was transferred to a blender, and 228.0 g of AVICEL® PH 101 microcrystalline cellulose (50 microns average particle size, FMC Corporation), 571.5 grams of urea (same as in Example 1), and 22.7 of Ac-Di-Sol® croscarmellose disintegrant were added. The resultant mixture was blended for five minutes. talc (40.4 g) and magnesium stearate (7.48 g) were added as lubricants and the mixture was blended for five minutes. This mixture was slugged using a vibratory screw feed which fed directly into the feed frame of a Colton 250 tablet press using a 1 and 13/16 inch flat face beveled edge punch. The slugged material was crushed in a Fitz mill fitted with a 12 USS mesh screen, providing a granular material. These granules were compressed on a Stokes Model R tablet press set at a rate of 16 tablets per minute. The tablet diameter was 2⅝ inches.

The 60 g tablets which were produced remained intact when dropped form a height of four feet to a hard surface indicating excellent hardness. The tablets disintegrated completely within 2 to 2.25 minutes when immersed in four liters of tap water at room temperature, demonstrating a disintegration rate acceptable for preparation of herbicide suspensions for spray application.

EXAMPLES 4–18

Other herbicide tablets were prepared essentially as described in Example 3 to determine the effects on hardness and disintegration time of compression force and of various proportions of MCC, urea and various additives. The data (Table 3) shows that both hard (high tensile strength) and soft (lower tensile strength) tablets can be produced with particulate blends of the invention but having disintegration (dissolving) times of similar magnitude, by varying the proportions of MCC and urea and by changing the amounts of lubricant and/or glidant (compare Examples 4, 6, 7, 9 and 10). Examples 10–14 show the effect of varying the compression force, in preparing the tablets, on disintegration times. It will be seen that lower hardness (tensile strength) leads to shorter disintegration times, and vice versa.

EXAMPLE 19

Pharmaceutically Active Spheres Prepared by Extrusion/Spheronization

Fast disintegrating spheres of hydrochlorothiazide (active) were prepared from the following formulation:

| Ingredients | Wt % | Wt/Wt |
|---|---|---|
| 1) Hydrochlorothiazide | 16.00 | 80 |
| 2) MCC/Urea (1:2) | 23.52 | |
| 3) Polyfon H Surfactant | 0.24 | 20 |
| 4) Ac-Di-Sol Croscarmellose | 0.24 | |
| 5) Dicalcium Phosphate | 57.00 | 285 |
| 6) Celatom FP4 Diatomite | 2.00 | 10 |
| 7) Ac-Di-Sol Croscarmellose | 1.00 | 5 |
| | 100.00 | 500 g |

The MCC/urea ingredient was a coprocessed material prepared by dissolving urea in water using a dispersator mixer, adding MCC in wetcake form to provide an MCC/urea weight ratio of 1:2, dispersing the MCC in the solution, and spray drying the mixture to form a powder having 2% (wt.) moisture content.

The Polyfon H surfactant (Westvaco) is a sodium lignosulfonate anionic dispersant. The Celatom FP4 diatomite is diatomaceous earth (Eagle-Picher). Ingredients 1–5 were blended in 2 quart Hobart mixer for 2 minutes at speed setting 1. Water, 140 ml, was added incrementally over a 3 minute period while mixing at speed setting 1. The wet mass was blended an extra 1 minute at speed setting 1 and then forced by hand through a 16 USS mesh screen and spheronized. The spheres were dried in a tray oven at 50° C. to 1% moisture level.

EXAMPLE 20

Wet Granulation Process—MCC/Ammonium Sulfate

AVICEL® PH 105 microcrystalline cellulose (MCC), 500 grams, and 320 grams of ammonium sulfate were mixed in a Hobart mixer at a slow speed for five minutes. While still mixing at a slow speed, a solution of 180 grams of ammonium sulfate in 375 grams of water was added portionwise during a one minute period. Care was taken to prevent solid build-up on the sides and paddle of the mixer. A wet, granular material that was a 1:1 blend of MCC/ammonium sulfate was formed. This material was screened using a 10 USS mesh screen. The screened material was then placed on trays and dried in a convection oven at 50° C. for six hours to bring the moisture content to 2–3%. The dry, granular material was screened through a 20 USS mesh screen. For those tablets containing a lubricant, the dry, screened granules were first placed in a "v" blender and blended for five minutes with about 10 grams (1% wt/wt) of magnesium stearate as lubricant. Similar tablets combining urea and the sulfate as nitrogen compounds were also prepared.

The dry, granular material, optionally containing the lubricant, was used to prepare 500 mg tablets using a Stokes Model B2 tablet press tooled with 7/16 inch standard concave punches. Tablet hardness was measured on a Schleuniger Hardness Tester. Tablet disintegration time was determined by immersing each tablet in approximately 700 mL of water at room temperature using a USP disintegration basket apparatus. Test results are given in Table 4 below in comparison with urea as the nitrogen compound. The good compressibility and disintegration times for tablets prepared with the MCC/ammonium sulfate composition indicate that the composition is an effective excipient for tabletting of active agents such as agricultural chemicals.

EXAMPLE 22

Particulate Blends Containing A Suspending Aid and Tablets Made Therewith

In a typical run, a slurry was prepared by combining, sequentially, 80 gallons of distilled water, 102 pounds of urea, 2.1 pounds of a food grade CMC (viscosity=25–50 centipoise at 2% concentration; degree of substitution=0.7) and 254 pounds of attrited MCC filtered wetcake (39% MCC in water). The slurry was passed once through an in-line colloid mill to fully disperse the solids prior to spray drying. The spray dryer conditions were adjusted to deliver a final particle size of about 30 to 50 μm and a water content of about 2–3%. The resultant powder was tabletted by the wet granulation method and disintegration time was determined, both as described in Example 2. A disintegration time of 5 minutes or less is considered optimum. Suspension numbers were determined by the CIPAC method MT-15 where the higher number indicates improved suspension. Tablets of MCC/urea without a suspending aid settle immediately upon disintegration in water and have a suspension number=0.

Test results are given in Table 5. It will be seen that both urea and CMC were necessary for good suspension and that the best formulation overall (fast disintegration and good suspension) is formulation 3.

TABLE 3

ATRAZINE:MCC:UREA TABLET FORMULATIONS
DRY-BLEND PROCESS
(% by weight)

| Ex. No. | Atrazine | MCC | Urea | Disintegrant[g] | Lubricant[a] | Glidant[b] | Surfactant[c] | Dispersant[d] | Tablet Tensile Strength[e] | Time[f] (sec) |
|---|---|---|---|---|---|---|---|---|---|---|
| 4 | 31.3 | 40.0 | 21.4 | 3.0 | 2.3[1] | 2.0[1] | — | — | 12.5 | 75 |
| 5 | 31.25 | 10.0 | 53.15 | 2.0 | 2.6[2] | 1.0[2] | — | — | 12.5 | 120 |
| 6 | 31.25 | 10.0 | 53.15 | 2.0 | 2.6[2] | 1.0[2] | — | — | 5.5 | 90 |
| 7 | 62.5 | 10.0 | 18.9 | 3.0 | 2.6[2] | 3.0[1] | — | — | 5.0 | 210 |
| 8 | 62.5 | 10.0 | 19.4 | 3.0 | 2.6[2] | 2.5[2] | — | — | 3.0 | 180 |
| 9 | 62.5 | 10.0 | 20.9 | 2.0 | 0.6[3] | 4.0[3] | — | — | 3.0 | 90 |
| 10 | 52.7 | 10.0 | 25.7 | 2.0 | 0.6[3] | 3.0[2] | 1.0 | 5.0 | 13.0 | 75 |
| 11 | 52.7 | 10.0 | 25.7 | 2.0 | 0.6[3] | 3.0[2] | 1.0 | 5.0 | 11.0 | 120 |
| 12 | 52.7 | 10.0 | 25.7 | 2.0 | 0.6[3] | 3.0[2] | 1.0 | 5.0 | 5.5 | 45 |
| 13 | 52.7 | 10.0 | 25.7 | 2.0 | 0.6[3] | 3.0[2] | 1.0 | 5.0 | 4.0 | 30 |
| 14 | 52.7 | 10.0 | 25.7 | 2.0 | 0.6[3] | 3.0[2] | 1.0 | 5.0 | 2.5 | 30 |
| 15 | 52.8 | 13.96 | 19.9 | 2.66 | 0.6[3] | 3.48[2] | 1.32 | 5.28 | | >120 |
| 16 | 52.7 | 10.0 | 25.7 | 2.0 | 0.6[3] | 3.0[2] | 1.0 | 5.0 | 1.5 | >120 |
| 17 | 51.85 | 9.84 | 25.29 | 2.97 | 1.2[4] | 2.95[1] | 0.98 | 4.92 | 6.0 | >120 |
| 18 | 54.46 | 12.7 | 24.0 | 1.41 | 2.3[1] | 1.59[1] | 0.59 | 2.95 | | 240 |

[a]Lubricants consisted of talc and/or magnesium stearate.
1 = 2.0% talc/0.3% Mg stearate
2 = 2.0% talc/0.6% Mg stearate
3 = Mg stearate only
4 = 1.0% talc/0.2% Mg stearate
[b]Glidants (synthetic silicas)
1 = aerogenic silica
2 = fumed silica
3 = 3.0% aerogenic silica/1% fumed silica
[c]Surfactant used as an alkylarylsulfonate
[d]Dispersant used was a sodium lignosulfonate
[e]Calculated as in Example 2.
[f]Measured as in Example 2.
[g]Ac-Di-SOL[R] croscarmellose

TABLE 4

Test Results on Examples 20 and 21

| Tablet Composition (% wt/wt)[3] | | | | | Tablet Tensile Strength (kg/cm$^2$) | Compression Force (kg) | Ejection force (kg) | Disintegration Time (Seconds) |
|---|---|---|---|---|---|---|---|---|
| MCC[1] | Urea | (NH4)2SO4 | (NH4)3PO4 | | | | | |
| 50 | 50 | — | — | Unlubricated | 6 | 202 | 3 | 8.9 |
| | | | | | 9 | 317 | 10 | 10.8 |
| | | | | | 12 | 426 | 18 | 11.5 |
| | | | | | 18 | 640 | 23 | 108.0 |
| | | | | Lubricated[2] | 5 | 198 | 4 | |
| | | | | | 9 | 333 | 5 | |
| | | | | | 13 | 508 | 5 | |
| | | | | | 18 | 808 | 5 | |
| 50 | 25 | 25 | — | Unlubricated | 4 | 213 | 17 | 7.0 |
| | | | | | 8 | 392 | 25 | 15.7 |
| | | | | | 12 | 517 | 28 | 32.0 |
| | | | | | 18 | 844 | 28 | 470.0 |
| | | | | Lubricated | 4 | 349 | 5 | |
| | | | | | 9 | 609 | 6 | |
| | | | | | 13 | 935 | 5 | |
| | | | | | 15 | 1460 | 4 | |
| 50 | — | 50 | — | Unlubricated | 4 | 195 | 23 | 24.0 |
| | | | | | 8 | 355 | 33 | 104.0 |
| | | | | | 12 | 512 | 35 | 147.0 |
| | | | | | 15 | 654 | 40 | 513.0 |
| | | | | Lubricated | 4 | 409 | 6 | |
| | | | | | 8 | 662 | 8 | |
| | | | | | 12 | 918 | 9 | |
| | | | | | 15 | — | — | |
| 25 | — | 75 | — | Unlubricated | 4 | 412 | — | 24.0 |
| | | | | | 8 | 686 | 35 | 27.0 |
| | | | | | 13 | 1031 | 57 | 29.0 |
| | | | | | 17 | 1287 | 64 | 72.0 |

TABLE 4-continued

Test Results on Examples 20 and 21

| Tablet Composition (% wt/wt)[3] | | | | | Tablet Tensile Strength (kg/cm²) | Compression Force (kg) | Ejection force (kg) | Disintegration Time (Seconds) |
|---|---|---|---|---|---|---|---|---|
| MCC[1] | Urea | (NH4)2SO4 | (NH4)3PO4 | | | | | |
|  |  |  |  | Lubricated | 4 | 675 | 1 |  |
|  |  |  |  |  | 8 | 1012 | 2 |  |
|  |  |  |  |  | 12 | 1556 | 2 |  |
|  |  |  |  |  | 16 | 1291 | 2 |  |
| 25 | 37.5 | 37.5 | — | Unlubricated | 5 | 293 | 14 | 516.0 |
|  |  |  |  |  | 8 | 534 | 20 | 1025.0 |
|  |  |  |  |  | 13 | 593 | 40 | 41.0 |
|  |  |  |  |  | 16 | 763 | 48 | 51.0 |
|  |  |  |  | Lubricated | 4 | 375 | 6 |  |
|  |  |  |  |  | 8 | 646 | 9 |  |
|  |  |  |  |  | 12 | 945 | 12 |  |
|  |  |  |  |  | 15 | 3620 | 27 |  |
| 25 | 75 | — | — | Unlubricated | 4 | 309 | 12 | 8.0 |
|  |  |  |  |  | 8 | 485 | 18 | 16.0 |
|  |  |  |  |  | 12 | 723 | 23 | 19.0 |
|  |  |  |  |  | 17 | 1115 | 24 | 67.0 |
|  |  |  |  | Lubricated | 4 | 608 | 5 |  |
|  |  |  |  |  | 8 | 1691 | 7 |  |
|  |  |  |  |  | 8 | 4927 | 9 |  |
| 50 | — | — | 50 | Unlubricated | 4 | 350 | 23 |  |
|  |  |  |  |  | 6 | 487 | 58 |  |
|  |  |  |  |  | 12 | 734 | 78 | ≦60[4] |
|  |  |  |  |  | 23 | 1273 | 97 |  |
|  |  |  |  | Lubricated | 4 | 408 | 6 |  |
|  |  |  |  |  | 9 | 711 | 8 |  |
|  |  |  |  |  | 15 | 1033 | 9 |  |
|  |  |  |  |  | 23 | 1584 | 10 |  |

[1]Avicel[R] PH105 microcrystalline cellulose (MCC) was used in MCC/UREA/(NH4)2SO4 tabletting. Avicel[R] PH101 microcrystalline was used in the MCC/(NH4)3PO4 tabletting.
[2]Tablets were lubricated with 1% (wt/wt) magnesium stearate.
[3]Tablets of 500 mg were prepared.
[4]Disintegration time was not determined by USP methods, but rather visually in 250 ml of water.

TABLE 5

Characteristics of Tablets Containing MCC, CMC and Urea

| Form- ulation | Composition (% wt/wt) | | | Tablet Hardness (kg) | Disintegration Time of Tablet (min.) | Suspension Number | Percent Residue On 100 Mesh Screen |
|---|---|---|---|---|---|---|---|
|  | MCC | CMC | Urea |  |  |  |  |
| 1 | 99.0[1] | 1.0 | — | Powder |  | 12.2 | — |
|  |  |  |  | 4 | <0.5 | 3.9 | 5.9 |
|  |  |  |  | 8 | <0.5 | 7.8 | 12.4 |
| 2 | 99.0[2] | 1.0 | — | Powder |  | 15.9 | — |
|  |  |  |  | 4 | <1.0 | 0.8 | 13.4 |
|  |  |  |  | 8 | <1.0 | 4.3 | 16.7 |
| 3 | 49.5[1] | 1.0 | 49.5 | Powder |  | 58.8 | 7.8 |
|  |  |  |  | 4 | <2.0 | 52.8 | 6.2 |
|  |  |  |  | 8 | <5.5 | 54.9 | 11.4 |
| 4 | 49.5[2] | 1.0 | 49.5 | Powder |  | 44.9 | — |
|  |  |  |  | 4 | <30.0 | 57.1 | 2.2 |
|  |  |  |  | 8 | <40.0 | 57.1 | 5.0 |

[1]Commercial MCC derived from northern softwoods by the sulfite process, having an alpha cellulose content of about 93% and attrited to a particle size of about 6 to 9 μm.
[2]Same MCC as 1 but having a particle size about 22 to 25 μm.

We claim:

1. A solid dosage form comprising a compacted particulate blend consisting essentially of (a) a compression moldable finely divided homogenous particulate mixture of from about 0.05 to about 25 percent of microcrystalline cellulose having a particle size of from about 20 microns to about 90 microns and a nitrogen compound selected from the group consisting of urea, ammonium sulfate and ammonium phosphate, in which the weight ratio of microcrystalline cellulose to nitrogen compound is from about 10:1 to about 1:10;

(b) from about 16 percent to about 65 percent of an active material compatible with the particulate mixture of (a) and selected from herbicides, plant growth regulators, pesticides and any mixtures thereof; and (c) 0 to about 20 percent of an additive selected from glidants, lubricants, dispersants, surfactants, and auxiliary disintegrants and mixtures thereof.

2. The particulate blend of claim 1 wherein the nitrogen compound is urea.

3. The particulate blend of claim 1 wherein the nitrogen compound is ammonium phosphate.

4. The particulate blend of claim 1 wherein the nitrogen compound is ammonium sulfate.

5. The particulate blend of claim 1 wherein the nitrogen compound is urea and the microcrystalline cellulose:urea ratio is from about 2:1 to about 1:3.

6. A solid dosage form as in claim 1 wherein the active agent is an agricultural chemical.

7. A solid dosage form as in claim 1 wherein the nitrogen compound is urea.

8. A solid dosage form as in claim 1 wherein the nitrogen compound is ammonium sulfate or ammonium phosphate.

9. A solid dosage form as in claim 1 wherein the nitrogen compound is urea, the active agent is an agricultural chemical, and the average particle size of the microcrystalline cellulose is in the range of about 20 to 90 microns.

10. A solid dosage form as in claim 1 wherein the active agent is a herbicide or pesticide, the nitrogen compound is urea, the microcrystalline cellulose:urea ratio of urea is about 2:1 to about 1:3, and the average particle size of the microcrystalline cellulose is in the range of about 20 to 90 microns.

11. A solid dosage form as in any one of claims 1 through 5 wherein the particulate blend includes from about 0.05% to about 2.5% based on the weight of microcrystalline cellulose of a suspending agent for the microcrystalline cellulose, selected from water-soluble hydrocolloids compatible with and effective for assisting in hydration of the microcrystalline cellulose.

12. A solid dosage form as in claim 11 wherein the suspending agent is sodium carboxymethylcellulose.

* * * * *